(12) United States Patent
Shiraiwa et al.

(10) Patent No.: US 6,443,314 B2
(45) Date of Patent: Sep. 3, 2002

(54) MEMBRANE FILTRATION SYSTEM

(75) Inventors: Kazuo Shiraiwa; Shin-ichi Waku, both of Tokyo; Masamichi Tawara; Yuichi Nishimura, both of Hiroshima, all of (JP)

(73) Assignee: Elmex Limited, Tokyo (JP)

( * ) Notice: Subject to any disclaimer, the term of this patent is extended or adjusted under 35 U.S.C. 154(b) by 53 days.

(21) Appl. No.: 09/792,048

(22) Filed: Feb. 26, 2001

(30) Foreign Application Priority Data

Feb. 25, 2000 (JP) ........................................ 2000-048552

(51) Int. Cl.$^7$ ........................... B01D 63/08; B01D 29/01
(52) U.S. Cl. .................. 210/474; 210/464; 210/321.75; 422/101; 435/297.5
(58) Field of Search ................................ 210/474, 464, 210/321.75; 422/99, 101; 435/297.1, 297.5

(56) References Cited

U.S. PATENT DOCUMENTS

| | | | |
|---|---|---|---|
| 4,301,010 A | | 11/1981 | Eddleman et al. |
| 4,614,585 A | | 9/1986 | Mehra et al. |
| 4,689,147 A | * | 8/1987 | Leoncavallo et al. |
| 4,767,602 A | * | 8/1988 | Johnson |
| 4,829,005 A | * | 5/1989 | Friedman et al. |
| 4,849,061 A | * | 7/1989 | Relyea |
| 5,308,483 A | | 5/1994 | Sklar et al. |
| 5,695,639 A | | 12/1997 | Johnson |
| 5,792,425 A | | 8/1998 | Clark et al. |
| 5,849,249 A | * | 12/1998 | Jones, Jr. et al. |
| 6,358,730 B1 | * | 3/2002 | Kane |

* cited by examiner

*Primary Examiner*—Ana Fortuna
(74) *Attorney, Agent, or Firm*—Rothwell, Figg Ernst & Manbeck (57) ABSTRACT

Disclosed is a membrane filter system comprising an integral plastic holder (1, 23) having a filter receiving section (2, 24) for receiving a membrane filter (3, 30) that collects target microorganism contained in sample solution, a funnel mount (9, 25) positioned at a level higher than the filter receiving section for carrying thereon a cup-shaped paper funnel (12, 33) adapted to receive the sample solution, and a drainage (7, 28) communicated with the filter receiving section. The funnel has a bottom sheet or a paper filter (14, 35) and a bottom peripheral flange (15, 36) surrounding the bottom sheet. Resin seal means (11, 22) is fitted to the funnel mount to provide liquid-tight engagement between the funnel and the holder. The bottom sheet of the funnel is positioned above the membrane filter and serves as a primary filter for collecting particles in the sample solution larger than the target microorganism before the sample solution reaches the membrane filter.

17 Claims, 8 Drawing Sheets

MEMBRANE FILTRATION SYSTEM

BACKGROUND OF THE INVENTION

1. Field of the Invention

The present invention relates to a membrane filter system including a membrane filter for use particularly in bacteriological examination and cultivation.

2. Description of the Prior Art

One of typical methods for bacteriological examination is referred to as a HGMF (hydrophobic grid membrane filter) method wherein sample solution is caused to pass through a membrane filter of biologically inactive material such as PES polyethersulfone and PVDF (polyvinylidene difluoride) so that microorganism or bacteria contained in the sample solution is caught by the membrane filter.

Some different systems have been proposed to conduct the bacteriological examination in accordance with the HGMF method. One system comprises a funnel and a storage bottle, both made of glass material, which are connected to each other by a cylindrical coupler including a membrane filter. With this system, a predetermined quantity of the sample solution poured into the funnel will flow down into the storage bottle, during which microorganism contained in the sample solution is caught by the membrane filter.

Another example to be used for the HGMF filtration system comprises a plurality of funnels, each provided with a membrane filter at the bottom thereof and connected to a manifold. The manifolds are all connected to a main pipe which is, in turn, connected to a storage bottle and a vacuum source. When a vacuum is applied to the manifolds through the main pipe, microorganism contained in sample solution in the respective funnels may be caught by the respective membrane filters at the same time.

The above-described and other prior art systems for use in the HGMF filtration usually employ a filter unit comprising a substantially dish-shaped filter holder made of plastic material such as PP(polypropylene) and PE (polyethylene) and a membrane filter detachably mounted to the bottom of the holder. After all the sample solution has passed through the unit, the unit is removed from the system and then the filter is removed from the holder of the unit. The filter carrying microorganism thereon is transferred to a laboratory dish filled with suitable culture medium for cultivation of the microorganism.

With the filter unit of the above-described type, the membrane filter tends to be soon clogged up with food leavings or any other impurities having particle diameter larger than the target microorganism.

A disposable filter unit has also been proposed, in which a membrane filter is fixedly mounted to the bottom of a funnel. In order to provide sufficient liquid-tight abutment between the funnel and the membrane filter, not only the funnel but also the membrane filter should be made of plastic material. Therefore, this filter unit of disposable type is easy to handle but should be too much expensive, which would be a bar to its popularization.

SUMMARY OF THE INVENTION

Accordingly, it is a principal object of the present invention to overcome the drawbacks and disadvantages of the prior art membrane filter system for use in the HGMF filtration in bacteriological examination.

Another object of the present invention is to provide a membrane filter unit of unique construction which is easy to handle and inexpensive to manufacture.

To achieve these and other objects, the present invention utilizes a paper funnel that can easily be purchased at a cost much lower than the plastic funnel used in the prior art membrane filter systems. More particularly, the present invention employs a paper funnel with a bottom which may be used as a paper filter. The bottom of the paper funnel will therefore serve as a primary filter to which the sample solution is first subjected before passing through the membrane filter. Microorganism of larger particles in the sample solution should be caught by the primary filter and collected on the bottom of the paper funnel, which eventually prevents clog-up of the membrane filter.

As stated above, the membrane filter unit of the present invention employs the paper funnel in place of the plastic funnel. However, the paper funnel is difficult to be liquid-tightly fitted to the membrane filter because of material difference therebetween. To cope with this problem, in accordance with the present invention, a bottom peripheral flange of the paper funnel is fitted to a ringed groove of a dish-shaped filter holder with resin seal means, to thereby provide liquid-tight engagement therebetween and prevent leakage of the sample solution.

In accordance with an aspect of the present invention, therefore, there is provided a membrane filter system comprising: an integral plastic holder having a filter receiving section, a funnel mount positioned at a level higher than the filter receiving section, and a drainage communicated with the filter receiving section; a membrane filter received in the filter receiving section for collecting target microorganism contained in sample solution; a cup-shaped paper funnel adapted to receive the sample solution, having a bottom sheet and a bottom peripheral flange surrounding the bottom sheet; and resin seal means fitted to the funnel mount to provide liquid-tight engagement between the funnel and the holder, wherein the bottom sheet of the funnel being positioned above the membrane filter, when the funnel is fitted to the funnel mount of the holder, to serve as a primary filter for collecting particles in the sample solution larger than the target microorganism before the sample solution reaches the membrane filter.

In this system, the filter receiving section preferably has a recess for receiving a sheet of porous material which supports thereon the membrane filter. The recess is preferably provided with a plurality of spaced projections for supporting thereon the porous material sheet. A preferable example of the porous material sheet is polypropylene or paper filter.

In one embodiment of the membrane filter system of the present invention, there is a double-wall construction at an upper peripheral portion of a plastic holder. The double-wall construction comprises an inner wall, an outer wall and a groove defined between the inner and outer walls. A bottom peripheral flange of a paper funnel is inserted into the groove which has been filled with liquid silicone resin or any suitable resin material, so that the funnel is liquid-tightly fitted to the holder when resin is hardened. This provides liquid-tight engagement between the paper funnel and the resin holder and prevents leakage of the sample solution to the outside of the system. This membrane filter system is manufactured as a disposable unit.

Accordingly, in accordance with another aspect of the present invention, there is provided a membrane filter system comprising: an integral plastic holder having a filter receiving section, a double-wall construction at an upper peripheral portion of the holder, including an inner wall, an outer wall and a groove defined between the inner and outer walls, a recess formed in the filter receiving section, and a drainage communicated with the recess; a membrane filter received in the filter receiving section for collecting target microorganism contained in sample solution; a cup-haped paper funnel adapted to receive the sample solution, having a bottom sheet and a bottom peripheral flange surrounding the bottom sheet; sealer material poured into the groove of the double-wall construction of the holder and hardened after the bottom peripheral flange of the funnel is inserted into the groove whereby the funnel is liquid-tightly fitted to the funnel; and a sheet of porous material received in the recess of the holder; wherein the bottom sheet of the funnel is positioned above the membrane filter, when the funnel is secured to the funnel by the hardened sealer material, to serve as a primary filter for collecting particles in the sample solution larger than the target microorganism before the sample solution reaches the membrane filter.

In this system, preferably, the holder has a ringed packing member fitted within the filter receiving section to hold down the membrane filter. The membrane filter may be in advance bonded to a bottom of the packing member into a filter unit, which is mounted onto the filter receiving section. A preferable sealer material to be poured into the groove of the double-wall construction of the holder is silicone resin.

In another embodiment of the membrane filter system of the present invention, an integrally formed plastic seal ring is used. A bottom peripheral flange of a paper funnel is fitted to the seal ring which is, in turn, fitted to a housing. This also provides liquid-tight engagement between the paper funnel and the resin holder and prevents leakage of the sample solution to the outside of the system. With this system, the seal ring is detachable with respect to the paper funnel, as well as to the holder.

Accordingly, the seal ring which is relatively expensive and is not directly contaminated by the sample solution during filtering operation is reusable. This reduces the overall costs required for repeat of biological examination.

Accordingly, in accordance with another aspect of the present invention, there is provided a membrane filter system comprising: an integral plastic holder having a filter receiving section, a funnel mount positioned at a level higher than the filter receiving section, a peripheral wall surrounding the funnel mount, and a drainage communicated with the filter receiving section; a membrane filter received in the filter receiving section for collecting target microorganism contained in sample solution; a cup-shaped paper funnel adapted to receive the sample solution, having a bottom sheet and a bottom peripheral flange surrounding the bottom sheet; and a seal ring of resin material that liquid-tightly engages the bottom peripheral flange of the funnel and is liquid-tightly mounted on the funnel mount of the holder within the peripheral wall, wherein the bottom sheet of the funnel being positioned above the membrane filter, when the funnel is fitted to the holder, to serve as a primary filter for collecting particles in the sample solution larger than the target microorganism before the sample solution reaches the membrane filter. The seal ring is typically made of silicone rubber.

In this system, the seal ring may be detachable with respect to the funnel, as well as to the holder. In a preferable embodiment, the seal ring has an inward extension that extends toward the filter receiving section for holding down a peripheral portion of the membrane filter received in the filter receiving section.

In another preferable embodiment of this system, the seal ring has a double-wall construction including an inner wall, an outer wall and a groove defined between the inner and outer walls for detachably engaging the bottom peripheral flange of the funnel. The seal ring is fitted to the funnel in a manner that the outer wall is engaged within the peripheral wall of the holder.

The peripheral wall of the holder may have a plurality of spaced, inward projections for engagement with a top of the seal ring. The peripheral wall of the holder may also have an outward projection.

In another preferable embodiment of this system, the membrane filter is superposed on a secondary filter sheet, both being received in the filter receiving section of the holder. The filter receiving section of the holder is may be provided with a plurality of spaced projections for supporting thereon the secondary filter sheet and the membrane filter.

BRIEF DESCRIPTION OF THE DRAWINGS

Other objects and advantages of the present invention can be understood from the following description when read in conjunction with the accompanying drawings in which.

DETAILED DESCRIPTION OF THE PREFERRED EMBODIMENT

Figure 1:
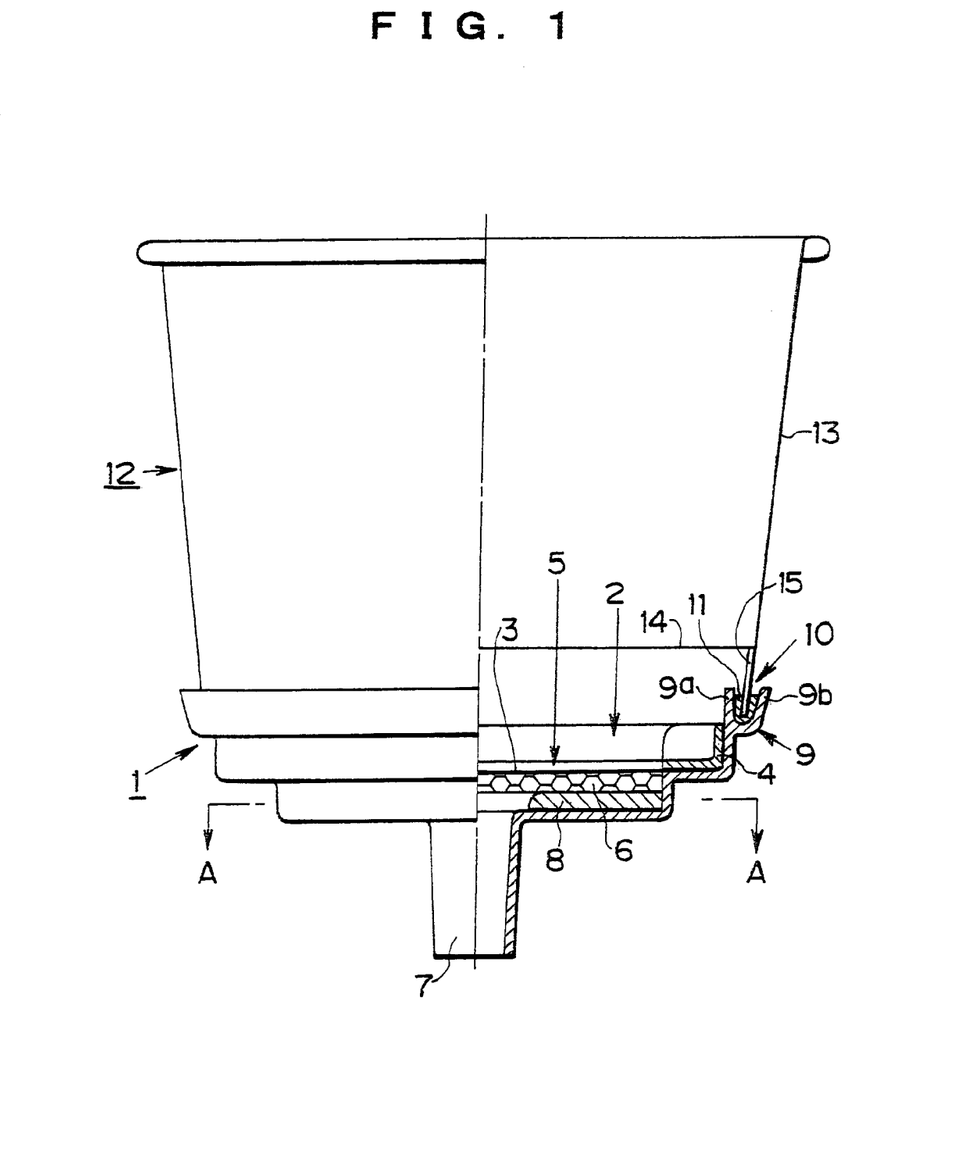
FIG. 1 is a front view, partly in longitudinal section, of a filter unit embodying the present invention.
Figure 2:
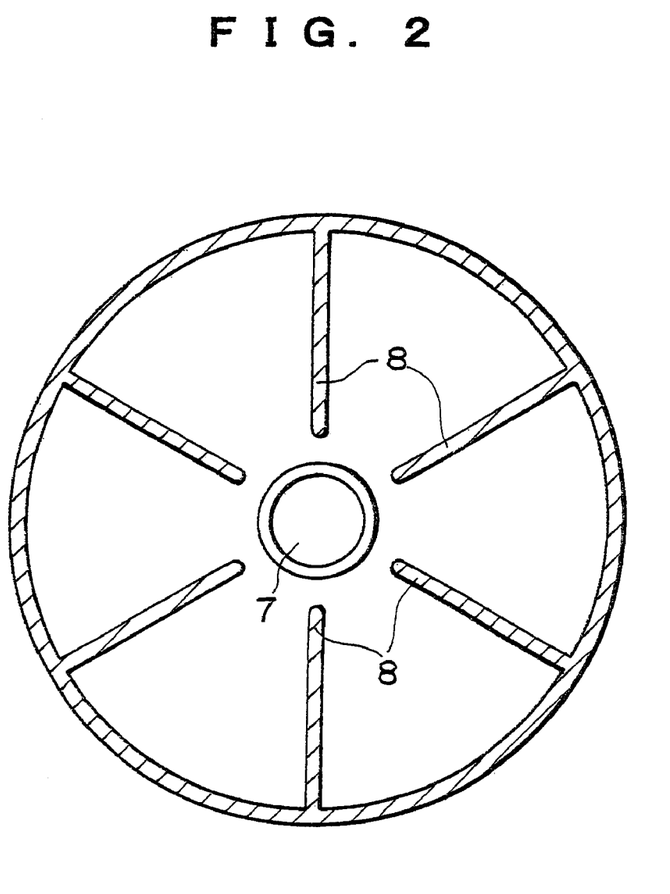
FIG. 2 is a cross-section taken along the lines A—A in FIG. 1.

Shown in FIGS. 1 and 2 is a disposable membrane filter unit embodying the present invention. This filter unit has a substantially dish-shaped filter holder 1 integrally formed from resin material such as PP (polypropylene), acrylic resin and HDPE (hi-density polyethylene), to which a membrane filter 3 is mounted, and a cup-shaped paper funnel 12 fixedly and inseparably secured to the holder 1. The membrane filter 3 is shown by a bold line in FIG. 1.

The holder 1 has a filter receiving section 2 for receiving the membrane filter 3 made of biologically inactive material such as PES polyethersulfone and PVDF (polyvinylidene difluoride), The peripheral portion of the membrane filter 3 is engaged by a packing ring 4 of resin material such as HIPS, which is also received in the section 2 in engagement with an upstanding wall surrounding the section 2, whereby the membrane filter 3 is kept in position.

The filter receiving section 2 has a concentric recess 5 of a smaller diameter for receiving porous material 6, which supports thereon the membrane filter 3. A drainage or drainpipe 7 is also an integral part of the holder 1, which communicates with the recess 5. In operation, the drainpipe 7 is connected to a vacuum pump (not shown) which applies a suction power to the membrane filter 3 via the porous material 6. Any kind of the porous material may be used, but PP and filter paper will be most preferable material to be used as the porous material 6 in this unit because of its low price.

To facilitate the vacuum suction, the porous material 6 is preferably supported on a plurality of spaced projections upstanding from the bottom of the recess 6. In this embodiment, a plurality of radially extending ribs 8 are provided with equal spacings of central angle of 60 degrees, which is best seen in FIG. 2. The ribs 8 are integral with the upstanding wall surrounding the section 2 but do not overlay the opening of the drainpipe 7.

The, peripheral portion of the holder 1 has a double-wall construction 9 having an inner wall 9a, an outer wall 9b and a ringed groove 10 which is filled with resin sealer material 11 such as silicone.

The paper funnel 12 is a paper cup which is easy to come by at very low price. A peripheral wall 13 of the paper funnel 12 extends down to provide a bottom peripheral flange or leg 15 which projects downward from a bottom sheet 14. The bottom peripheral flange 15 is inserted into the groove 10 in the double-wall construction 9 of the holder 1, and fixed thereat by means of the hardened silicone sealer 11 filled also in the groove 10.

The bottom sheet 14 of the paper funnel 12 is a paper filter of 100 micron mesh, for example, which will serve as a primary filter for collecting particles in sample solution in the funnel 12 larger than the target microorganism, before the sample solution reaches the membrane filter 3 which is positioned below the funnel 12.

The filter unit of the above construction is assembled as follows. The holder 1 is formed from PP or acrylic resin or any other suitable resin into an integral product of a predetermined shape having the filter receiving section 2, the recess 5, the drainpipe 7 and the double-wall construction 9. The porous material 6 such as PP and filter paper is placed within the recess 5, and the membrane filter 3 and the packing ring 4 are placed on the porous material 6 within the filter receiving section 2. Meanwhile, silicone sealer 11 in a liquid state is poured into the groove 10 in the double-wall construction 9, into which the bottom peripheral flange 15 of the paper funnel 12 is inserted. When the silicone sealer 11 in the groove 10 is hardened, the paper funnel 12 is fixedly secured to the holder 1 into a one-piece, disposable filter unit as shown in FIG. 1.

In preferable application, the peripheral portion of the membrane filter 3 is in advance bonded to the bottom of the packing ring 4 into a filter assembly, which is picked up with tweezers and placed onto the porous material 6.

After manufacturing a plurality of the filter units in a manner described above, they are air-tightly wrapped with a film of air-impermeable resin material, one by one. Then, a predetermined number (300, for example) of the wrapped units are packed in a cardboard box, which is put on the market after being sterilized with irradiation of gamma rays of 15KGY, for example.

In operation, the drainpipe 7 is connected to the vacuum pump (not shown) to apply a predetermined suction power to the membrane filter 3, and the sample solution containing the target microorganism which is the subject of the biological examination is poured into the funnel 12 at a predetermined flow rate. Any particle, including food leavings, larger than that of the target microorganism or bacteria could not pass through the funnel bottom sheet 14 of 100 micron mesh which acts as the primary filter and, therefore, collected on the bottom 14. This effectively prevents clog-up of the membrane filter 3.

The sample solution which successfully have passed through the funnel bottom 14 will then reach the membrane filter 3. The target microorganism, that is bacteria of 1–4 micron diameter, for example, contained in the sample solution is caught by the membrane filter 3. The solution passing through the membrane filter 3 will then pass through the porous material 6 and flow down through the drainpipe 7 into a tank (not shown) or to be discharged to the outside of the system.

While the sample solution in the funnel 12 is subjected to the suction power to flow down toward the drainpipe 7, a part of thereof could overflow the inner wall 9a into the groove 10 of the double-wall construction 9 of the holder 1. However, no leakage to the outside of the system should occur because of liquid-tight engagement between the funnel bottom flange 15 and the double-wall construction 9 of the holder 1 by means of the hardened silicone sealer 11.

After all of the sample solution has passed through the membrane filter 3, the packing ring 4 is picked up with tweezers so that the membrane filter 3 attached thereto is removed from the holder 1. The membrane filter 3 is placed in a laboratory dish (not shown) containing a suitable culture medium where the target bacteria carried by the filter 3 is cultivated for biological examination.

In the above-described filter unit, the silicone or other resin sealer 11 is poured into the groove 10 and then hardened, which provides liquid-tight engagement between the funnel 12 and the holder 1. In a modification, an elastic seal ring formed into a predetermined configuration from resin material such as silicone rubber is fitted within the groove 10. An example of such elastic seal ring 16 is shown in FIGS. 3 and 4.

This seal ring 16 is generally configured such that it may be elastically and liquid-tightly fitted within the groove 10. In addition, the periphery of the seal ring 16 extends outwardly to define a groove 17 and a downward extension 18. The seal ring 16 is mounted to the double-wall construction 9 in such a manner that the groove 17 receives the outer wall 9b. The bottom of the seal ring 16 has an inner projection 19 and an outer projection 20 at opposite ends, which provide elastic engagement with the inner and outer walls 9a, 9b of the double-wall construction 9, which improves liquid-tight fitting of the seal ring 16 with respect to the groove 10. The seal ring 16 also has an upward groove 21 to which the bottom peripheral flange 15 is fittingly insertable.

With the above construction, the seal ring 16 is liquid-tightly fitted within the groove and, in turn, adapted to liquid-tightly receive the funnel flange 15. In other words, the holder 1 and the funnel 12 are in liquid-tight engagement by means of elasticity of the seal ring 16 fitted within the groove 10. However, the seal ring 16 is detachable with respect to either of the holder 1 and the seal ring 16. Accordingly, the holder 1 and the funnel 12 may be reused after being sterilized with pressurized steam in an autoclave.

Figure 3:
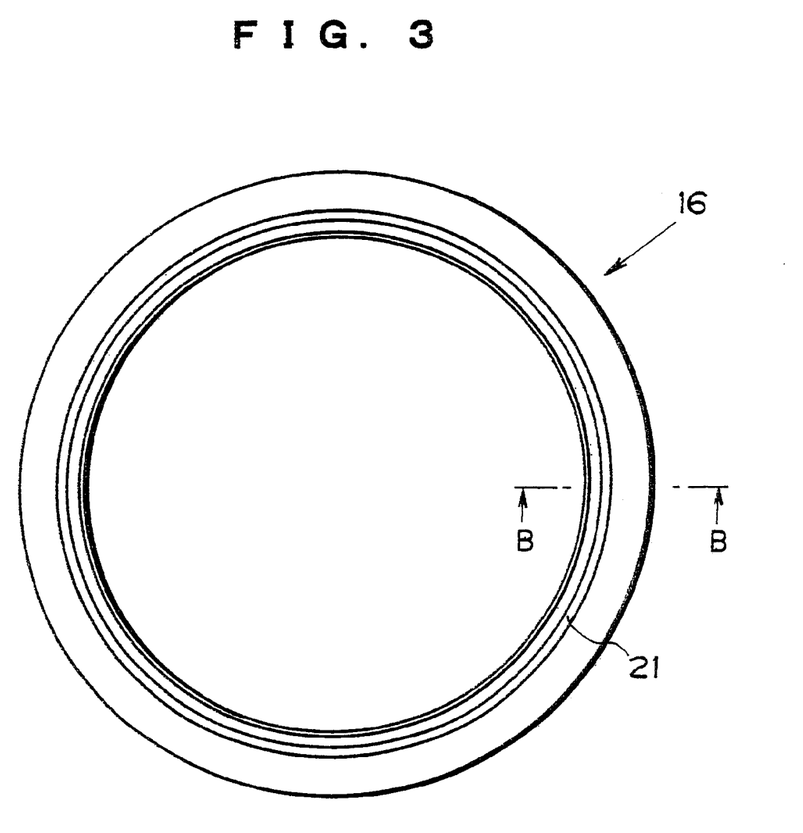
FIG. 3 is a top view showing an example of a seal ring fittable into a groove of a double-wall construction of a filter holder of the unit shown in FIG. 1.
Figure 4:
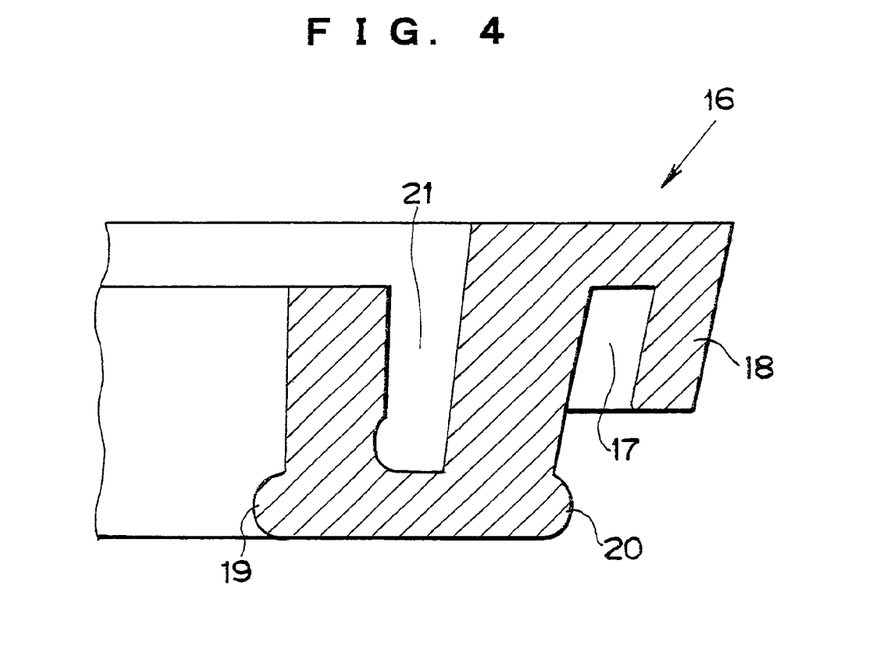
FIG. 4 is a cross-section, on an enlarged scale, taken along the lines B—B in FIG. 3.
Figure 5:
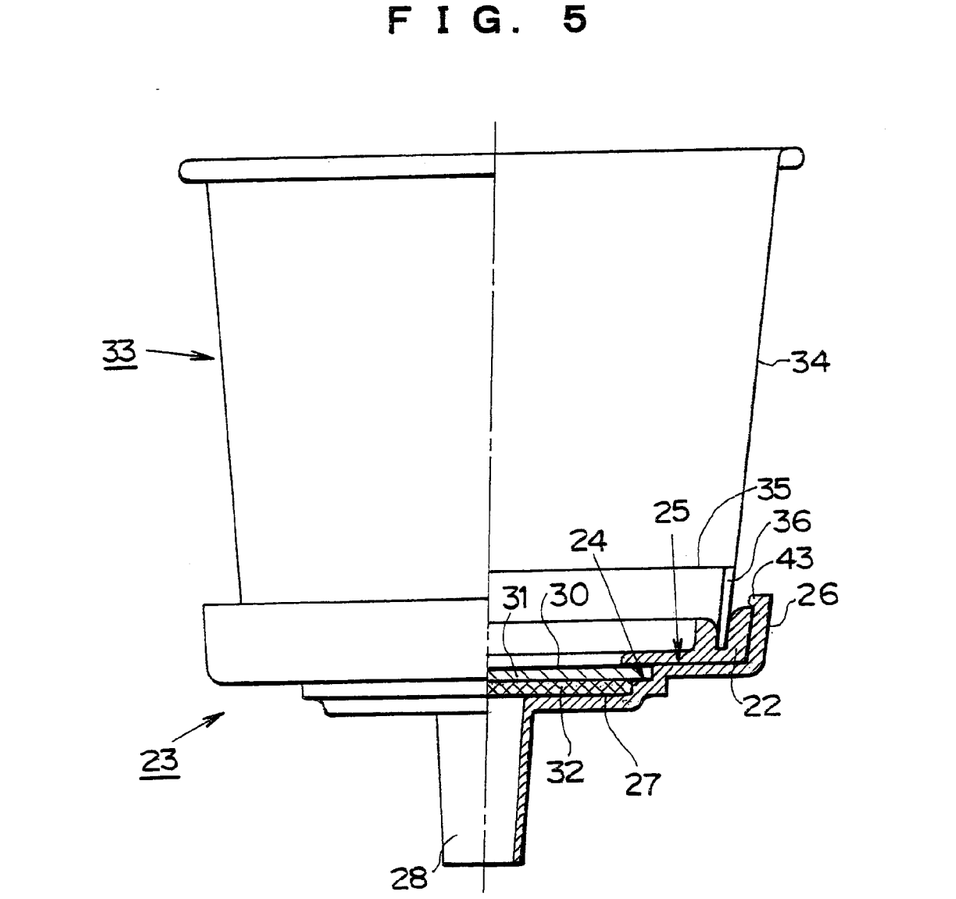
FIG. 5 is a front view, partly in longitudinal section, of a filter unit according another embodiment of the present invention.

Shown in FIG. 5 is a membrane filter unit of reusable type which also embodies the present invention, in which a seal ring of silicon rubber 22 with some modifications from the seal ring 16 of FIGS. 3 and 4.

A filter holder 23 is an integrally formed product of PP, acrylic resin, HDPE or any other suitable resin material, having a filter receiving section 24, a funnel mount 25 surrounding the filter receiving section 24 and positioned at a level slightly higher than the section 24, a peripheral wall 26 surrounding the funnel mount 25 and a drainpipe 28 communicating with the filter receiving section 24.

A membrane filter 30, shown by a bold line in FIG. 5, is made of biologically inactive material such as PES and PVDF, which is placed in the filter receiving section 24. In this embodiment, a paper filter of approximately 1 mm thickness underlies the membrane filter 30, both being received within the filter receiving section 24. The peripheral portion of the membrane filter 30 is engaged by an inward extension 37 (FIG. 6) of the silicone rubber seal ring 22, so that the membrane filter 30 and the paper filter 31 may be prevented from floating displacement and maintained in position in the section 24.

The filter receiving section 24 has a concentric recess 27 of a smaller diameter where there are formed a plurality of spaced projections 32 for supporting thereon the filter paper 31 and the membrane filter 30. The projections 32 provide a common horizontal plane which is substantially co-planar with the bottom of the filter receiving section. Thus, the paper filter 31 and the membrane filter 30 are interposed, under elastic downward pressure caused by the seam ring 22, between the projections 32 and the inward extension 37 of the seal ring 22.

Figure 8:
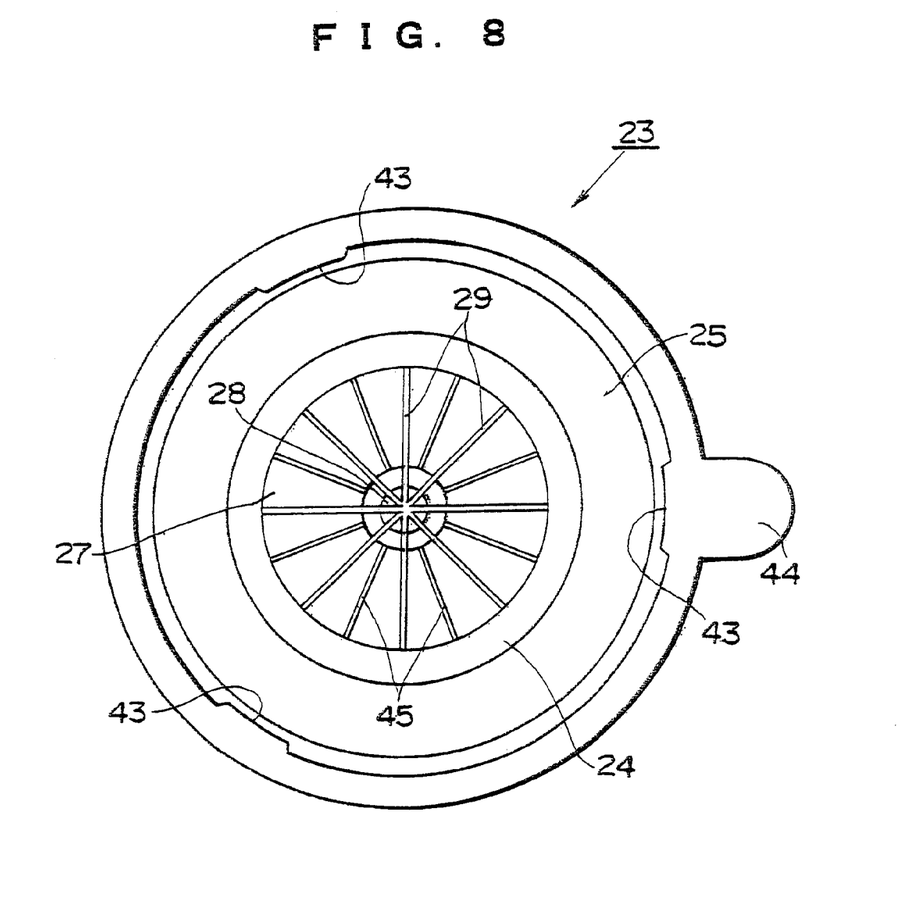
FIG. 8 is a top view showing a modification of a filter housing of the unit of FIG. 5.

The function of the projections 32 is similar to the ribs 8 in the foregoing embodiment of FIGS. 1 and 2. In this embodiment, however, the thin paper filter 31 is used as the porous material, which tends to be sucked into the drainpipe 28 when a vacuum power is applied. To prevent this phenomenon and keep the paper filter 31 (and the membrane filter 30) in position, the projections 32 should preferably comprise ribs 29 extending radially across the opening of the drainpipe 28, as shown in FIG. 8. In the example of FIG. 8, the radially extending ribs 29 are mounted at equal spacings of a central angle of 45 degrees. It is understood that this is only an example of the rib arrangement. Of course, there may be a greater number of the ribs 29 at smaller spacings. In addition to the ribs 29 extending across the drainpipe 28, it is preferable that the projections 32 further includes radial ribs 45 which only extend within the area of the recess 27 and do not overlie the opening of the drainpipe 28, as shown also in FIG. 8. In the illustrated embodiment, the ribs 45 are spaced equally with a central angle of 45 degrees and positioned in the middle of adjacent two of the ribs 29. The surfaces of the ribs 29 and 45 are substantially co-planar with each other and with the bottom of the filter receiving section 24.

A paper funnel 33 is mounted on the funnel mount 25 and engaged within the peripheral wall 26 of the holder 23. In this embodiment, the seal ring 22 which is detachable with respect to the holder 23 and the funnel 33 respectively is used to provide removable, but still liquid-tight engagement between the funnel 33 and the holder 23.

The paper funnel 33 used in this embodiment is similar to the paper funnel 12 used in the embodiment of FIGS. 1 and 2. The funnel is a commercial paper cup having a peripheral wall 34, a bottom 35 and a flange 36 which is an extension of the wall 34 and projects downward from the bottom 35. The bottom 35 comprises a paper filter of 100 micron mesh, for example, which will serve as a primary filter for collecting particles in sample solution in the funnel 33 larger than the target microorganism, before the sample solution reaches the membrane filter 30 which is positioned below the funnel 33.

Figure 6:
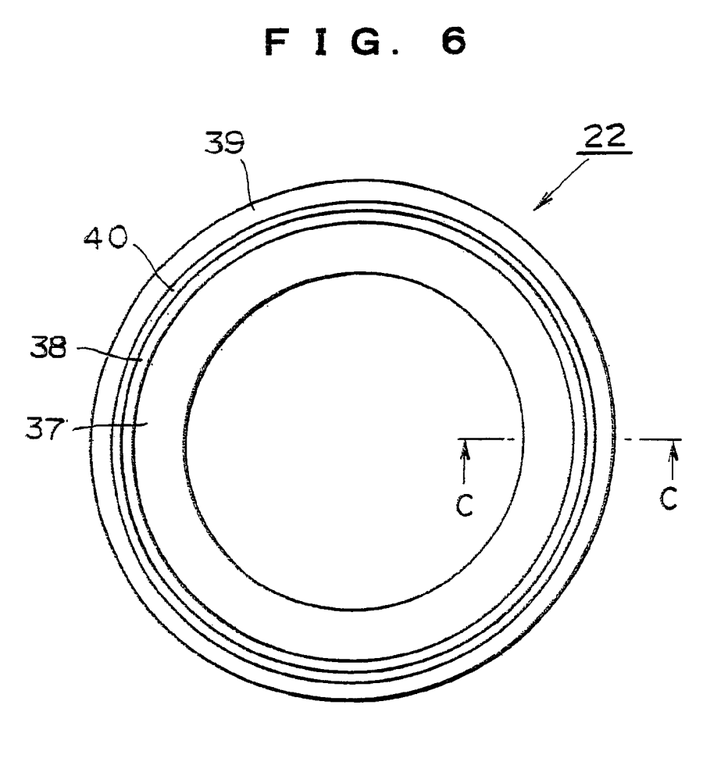
FIG. 6 is a top view of a seal ring employed in the unit of FIG. 5.
Figure 7:
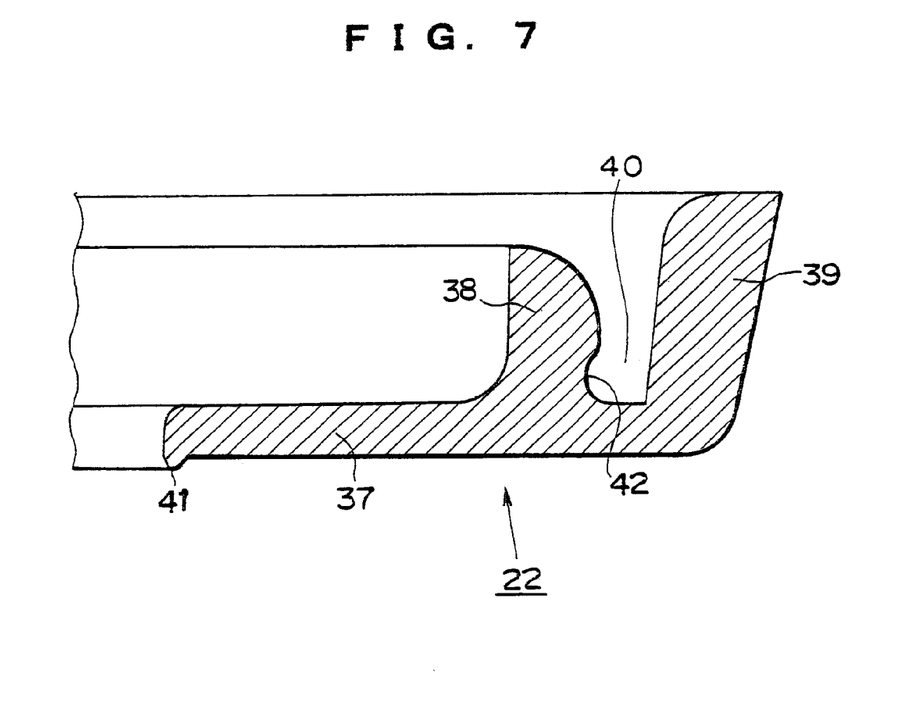
FIG. 7 is a cross-section, on an enlarged scale, taken along the lines C—C in FIG. 6.

Now referring specifically to FIGS. 6 and 7, the seal ring 22 is an integral product of silicone rubber, having a bottom 37 adapted to be placed on the funnel mount 25 of the holder 23, an inner wall 38 and an outer wall 39, each upstanding from the bottom 37 with an upward groove 40 therebetween. When the bottom 37 is placed on the funnel mount 25, the outer wall 39 is brought into elastic and close engagement with the internal surface of the holder wall 26. The groove 40 provides a diameter substantially equal to that of the bottom peripheral flange 36 of the paper funnel 33. Accordingly, the seal ring 22 may be mounted on the funnel mount 25 and elastically engaged within the peripheral wall 26 of the holder 23. The bottom flange 36 of the funnel 36 is inserted into the groove 43 before or after the seal ring 22 is fitted to the holder 23.

The filter unit of this embodiment is manufactured as follows. The holder 23 is formed from PP or acrylic resin or any other suitable resin into an integral product having the above configuration with the filter receiving section 24, the funnel mount 25, the peripheral wall 26, the recess 27 and the drainpipe 28. On the ribs 32 (which may comprise the ribs 29 and 45 shown in FIG. 8) is placed the paper filter 31 alone. At this time, nothing may be placed on the ribs 32.

Meanwhile, the bottom peripheral flange 36 of the paper funnel 33 is inserted into the groove 40 of the seal ring 22, which is then mounted onto the funnel mount 25 and engaged within the peripheral wall 26 of the holder 23. This assembly is substantially the same as that shown in FIG. 5 expect that there is no membrane filter 30 (and no paper filter 31). This assembly is sterilized with high-temperature, pressurized steam in an autoclave. The seal ring 22 and the paper funnel 33 are removed and the membrane filter 30 is picked up with tweezers and placed onto the paper filter 31. When nothing has been placed onto the ribs 32, the paper filter 31 and the membrane filter 30 are placed onto the ribs 32. Then, the seal ring 22 carrying the paper funnel 33 is fitted onto the funnel mount 25. Thus, the filter unit of FIG. 5 is manufactured. The membrane filter 30 is in advance sterilized and hermetically sealed in an air-tight bag.

The bottom 37 of the seal ring extends inwardly to cover the peripheral portion of the membrane filter 30 and, therefore, keep the membrane filter 30 in position fitted within the filter receiving section 27. A downward projection 41 (FIG. 7) at the inner edge of the bottom 37 of the seal ring 22 will exert a downward press onto the membrane filter 30 for more stable positioning thereof. For smooth insertion of the bottom peripheral flange 36 of the paper funnel 33 into the groove 40 of the seal ring 22, the bottom of the groove 40 may be provided with a side recess 42 (FIG. 7) at one or opposite walls of the groove 40.

The peripheral wall 26 of the holder 23 has a plurality of spaced, inward projections 43 at the top, which comes into engagement with the top of the outer wall 39 of the seal ring 22, when the seal ring 22 is fitted onto the funnel mount 25. The projections 43 act as stopper means for preventing the seal ring 22 from being inadvertently detached out of the holder 23. The projection 43 may extend over the entire circumference of the peripheral wall 26. However, such circumferential projection would be a bar to insertion of the seal ring 22 into the holder 23. It is, therefore, preferable that there are plural projections 43 at equal spacings of 120 degrees, for example, as best seen in FIG. 8.

The top of the peripheral wall 26 of the holder 23 partly extends outwardly to provide a tab 44, as shown in FIG. 8, which may be held between fingers for easier removal of the seal ring 22 from the holder 23.

The holder 23 and the seal ring 22 are both made of autoclavablee resin material and removable with each other. Accordingly, these parts may reused.

Although the present invention has been described in conjunction with several embodiments thereof, it is to be understood to a man skilled in the art that the present invention is not limited to the embodiments described and illustrated herein and many modifications and variations may be made without departing from the scope of the invention as defined in the appended claims.

For example, although the paper filter 31 is used to carry thereon the membrane filter 30, both being placed onto the ribs 32, in the embodiment of FIG. 5, the paper filter 31 is not always necessary. The membrane filter 30 alone may be placed on the ribs 32, which is also within the scope of the present invention. However, since the membrane filter 30 is generally expensive, it is preferable that the membrane filter of a smaller thickness s used in the filter system of the present invention. To achieve this, the paper filter that is easy to come by at a lower price should preferably be used in combination with the membrane filter. In some kind of biological examination, the paper filter impregnated with liquid medium may be used.

Although the present invention is particularly useful in biological examination of bacteria or microorganism contained in sample solution, it is applicable to any fluid. For example, the membrane filter system of the present invention may be used for measurement of cleanness of air (in a clean room). In this application, an air flow enters the paper funnel and passes through the membrane filter which entraps and collects the target bacteria in the air flow. The membrane filter is placed on a laboratory dish filled with suitable culture medium. After cultivation for a predetermined period, the number of bacteria in the culture medium is measured to determine cleanliness.

What is claimed is:

1. A membrane filter system comprising:
    an integral plastic holder having a filter receiving section, a funnel mount positioned at a level higher than said filter receiving section, and a drainage communicated with said filter receiving section;
    a membrane filter received in said filter receiving section for collecting target microorganism contained in sample solution;
    a cup-shaped paper funnel adapted to receive said sample solution, having a bottom sheet and a bottom peripheral flange surrounding said bottom sheet; and
    resin seal means fitted to said funnel mount to provide liquid-tight engagement between said funnel and said holder;
    said bottom sheet of said funnel being positioned above said membrane filter, when said funnel is fitted to said funnel mount of said holder, to serve as a primary filter for collecting particles in said sample solution larger than said target microorganism before said sample solution reaches said membrane filter.

2. A system according to claim 1 wherein said filter receiving section has a recess for receiving a sheet of porous material which supports thereon said membrane filter.

3. A system according to claim 2 wherein said recess is provided with a plurality of spaced projections for supporting thereon said porous material sheet.

4. A system according to claim 2 wherein said porous material is polypropylene or paper filter.

5. A membrane filter system comprising:
    an integral plastic holder having a filter receiving section, a double-wall construction at an upper peripheral portion of said holder, including an inner wall, an outer wall and a groove defined between said inner and outer walls, a recess formed in said filter receiving section, and a drainage communicated with said recess;
    a membrane filter received in said filter receiving section for collecting target microorganism contained in sample solution;
    a cup-shaped paper funnel adapted to receive said sample solution, having a bottom sheet and a bottom peripheral flange surrounding said bottom sheet;
    sealer material poured into said groove of said double-wall construction of said holder and hardened after said bottom peripheral flange of said funnel is inserted into said groove whereby said funnel is liquid-tightly fitted to said funnel; and
    a sheet of porous material received in said recess of said holder;
    said bottom sheet of said funnel being positioned above said membrane filter, when said funnel is secured to said funnel by said hardened sealer material, to serve as a primary filter for collecting particles in said sample solution larger than said target microorganism before said sample solution reaches said membrane filter.

6. A system according to claim 5 wherein said holder has a ringed packing member fitted within said filter receiving section to hold down said membrane filter.

7. A system according to claim 6 wherein said membrane filter is in advance bonded to a bottom of said packing member into a filter unit, which is mounted onto said filter receiving section.

8. A system according to claim 5 wherein said sealer material poured into said groove of said double-wall construction of said holder is silicone resin.

9. A membrane filter system comprising:
    an integral plastic holder having a filter receiving section, a funnel mount positioned at a level higher than said filter receiving section, a peripheral wall surrounding said funnel mount, and a drainage communicated with said filter receiving section;
    a membrane filter received in said filter receiving section for collecting target microorganism contained in sample solution;
    a cup-shaped paper funnel adapted to receive said sample solution, having a bottom sheet and a bottom peripheral flange surrounding said bottom sheet; and
    a seal ring of resin material that liquid-tightly engages said bottom peripheral flange of said funnel and is liquid-tightly mounted on said funnel mount of said holder within said peripheral wall;
    said bottom sheet of the funnel being positioned above said membrane filter, when said funnel is fitted to said holder, to serve as a primary filter for collecting particles in said sample solution larger than said target microorganism before said sample solution reaches said membrane filter.

10. A system according to claim 9 wherein said seal ring is detachable with respect to said funnel, as well as to said holder.

11. A system according to claim 9 wherein said seal ring has an inward extension that extends toward said filter receiving section for holding down a peripheral portion of said membrane filter received in said filter receiving section.

12. A system according to claim 9 wherein said seal ring has a double-wall construction including an inner wall, an outer wall and a groove defined between said inner and outer walls for detachably engaging said bottom peripheral flange of said funnel, said seal ring being fitted to said funnel in a manner that said outer wall is engaged within said peripheral wall of said holder.

13. A system according to claim 9 wherein said seal ring is made of silicone rubber.

14. A system according to claim 9 wherein said peripheral wall of said holder has a plurality of spaced, inward projections for engagement with a top of said seal ring.

15. A system according to claim 9 wherein said peripheral wall of said holder has an outward projection.

16. A system according to claim 9 wherein said membrane filter is superposed on a secondary filter sheet, both being received in said filter receiving section of said holder.

17. A system according to claim 16 wherein said filter receiving section of said holder is provided with a plurality of spaced projections for supporting thereon said secondary filter sheet and said membrane filter.

* * * * *